United States Patent [19]
Sweet

[11] Patent Number: 5,488,227
[45] Date of Patent: Jan. 30, 1996

[54] GAS ANALYZER

[75] Inventor: Christopher R. Sweet, Leicestershire, England

[73] Assignee: Geotechnical Instruments (UK) Limited, United Kingdom

[21] Appl. No.: 320,674

[22] Filed: Oct. 11, 1994

[30]  Foreign Application Priority Data

Oct. 8, 1993 [GB] United Kingdom .................. 9320756

[51] Int. Cl.⁶ .................................................. G01N 21/61
[52] U.S. Cl. .......................... 250/343; 250/347; 356/246
[58] Field of Search ..................... 250/343, 347, 250/353; 356/246, 440, 409, 439

[56]  References Cited

U.S. PATENT DOCUMENTS

3,319,071  5/1967  Werth et al. .
4,787,750  11/1988  Nelson et al. .......................... 356/439
4,795,253  1/1989  Sandridge et al. ................... 250/338.5
5,116,120  5/1992  Picker .
5,220,402  6/1993  Harvey .
5,222,389  6/1993  Wong .

*Primary Examiner*—Davis L. Willis
*Assistant Examiner*—Richard Hanig
*Attorney, Agent, or Firm*—Clifford W. Browning; Woodard, Emhardt, Naughton, Moriarty & McNett

[57]  ABSTRACT

A gas analyser and detector has an infra red source, a gas chamber and a detector cell; the detector cell has a gas sample inlet, inlet and exit paths for an infra red beam and reflector means in the chamber comprising a convex surface and a concave surface. The reflector means ensures a long path length for the beam whilst reducing beam divergence and signal loss.

19 Claims, 6 Drawing Sheets

GAS ANALYZER

This invention relates to an apparatus for determining the constituents of a gas, and for determining the concentration of particular constituents of the gas.

Gas detectors have been known for many years and are used in industry and commerce for the analysis of samples and to find leakages which otherwise cannot be detected. Many detectors comprise fixed installations which raise an alarm if concentration of a particular gas rises above a predetermined limit. For example such detectors are used in coal mines to warn of potentially explosive gas mixtures.

In recent times a demand has arisen also for a detector which can detect a range of different gases within a mixture, and their respective concentrations. Such a detector is useful for example where gas is collected from a landfill site for combustion in a power generator. The gas detector provides an analysis which permits the calorific value of the gas to be determined, and also provides information on gas concentrations which permits the gas to be burned in the most economical and environmentally friendly manner. These detectors are usually fixed installations and have no overall size constraints.

A demand has also arisen for gas sniffers which detect concentrations of a particular gas in air and in the parts per million range. Such detectors may for example be mounted in a van which travels along roads seeking leaks from buried gas pipes.

Many of these prior art detectors are designed to detect only a particular gas or range of gases in a predetermined concentration band. Typically the detector apparatus comprises an infra-red source, a gas chamber and detector cell designed to sense absorption by the gas of infra-red radiation in a particular wavelength band. It is known that particular gases absorb infra-red radiation in distinctive patterns, and that the absorbtion characteristic is different for each gas. By choosing particular wavelength bands, the presence of a particular gas and its concentration can be determined. This is the principle on which many gas detectors work.

An important constraint in gas detectors is that the infra-red path length must be sufficiently long to ensure that a measurable proportion of the infra-red radiation has been absorbed. The relationship between path length and the amount of radiation absorbed is of a generally logarithmic form and thus it is impractical to resolve all concentrations with a single path length of infra-red radiation. Instead the path length is chosen to ensure a given percentage absorption, for example in the range 10%–90%; this range will depend on the concentration of gas present and can be found empirically. In general only a short path length is required to detect a high concentration of a particular gas, whereas a long path length is required where the gas concentration is low.

The main practical constraint in determining the size of a gas detector is usually the means by which an effective path length (typically in the range 0.1–2 m) is provided.

Known gas detectors use reflection surfaces to bounce an infra-red beam from a source to a detector cell. U.S. Pat. No. 5,116,120 discloses for example a spherical gas chamber having windows to receive a radiation beam from a source, and to pass the beam to a sensor. The position of the windows is carefully chosen to ensure that the multiple beam reflections within the test chamber give the desired test distance. The entrance window is large, and by changing the relative angle of the incident beam, the number of reflections can be changed to provide different test lengths. The spherical test chamber is journalled for rotation in three mutually perpendicular planes to permit the incident angle of the beam to be varied. Rotation about the three mutually perpendicular axes by stepper motor is proposed, and the stepper motors may be activated according to pre-programming of a computerised control device.

Although this device can be physically small, it has a number of disadvantages; the spherical test chamber is difficult and expensive to manufacture, and the method of mounting the chamber for rotation is complex and requires three motors. The multiple reflections may interfere with one another, and the test distance is not progressively adjustable since each new distance is likely to require movement of all three motors—this inevitably means that the device must be manufactured to very close tolerances for good repeatability and reliability. The minimum change in test distance is probably about twice the internal diameter of the sphere, but may reduce with an increased number of reflections.

Moreover, most chambers having a concave reflection surface are dispersive, that is to say the beam tends to diverge on each reflection. As a result such detectors require very sensitive infra-red sensors (which are both expensive, and have a narrow detection range) or require use of a very powerful infra-red source (which is rather unsuitable for portable, hand held devices).

Another problem with prior art sample cells having concave reflection surfaces is that the beam is frequently considered to be of infinitely small cross sectional area; reflection paths are thus represented by lines. In a practical detector a beam will have significant area and will tend to diverge on reflection so that after only a few traverses of the cell, the beam is so wide that a significant proportion never reaches the infra-red sensor. Thus many sample cells which suggest the use of multiple reflections to achieve a long beam length are in fact impractical because signal loss is very large and thus rather expensive detectors are required; it can also be difficult to detect the beam due to the large amount of background 'noise'.

What is needed is a detector which can determine the presence and concentration of different gases in unknown quantities; be small, accurate, transportable and robust enough for hand held use under adverse conditions; and be relatively simple and economical to manufacture. The detector should have a sample chamber which is small since sample volumes are often small, and have predictable path length control.

According to the present invention there is provided a sample chamber for a gas detector, the chamber having a gas sample inlet, and defining an inlet path for a beam of energy, an exit path for said beam of energy and reflector means whereby the beam of energy is in use reflected from said inlet path to said exit path, said reflector means including a concave reflector surface and a convex reflector surface.

In a preferred embodiment the convex and concave surfaces may be of constant radius, and may be concentric; two dimensional curved surfaces are relatively easy to manufacture on conventional machine tools, and can thus provide accurate reflectors at an economical cost. The inlet path and exit path may be defined by openings in the convex and concave surfaces. The convex and concave surfaces may alternatively be curved in three dimensions, and in a preferred embodiment are part-spherical.

In a preferred embodiment the convex and concave surfaces are substantially circular, the inlet path being defined by the convex surface and the outlet path being defined by the concave surface. The inlet and outlet paths may alternatively be provided by the concave and convex surfaces respectively.

One or both of the concave and convex surfaces may be movable relative to the other surface to change the path length between inlet path and outlet path. Preferably the concave and convex surfaces are movable arcuately with respect to one another, and in the most preferred embodiment the surfaces are relatively rotatable about a common axis.

The concave surface may comprise an outer wall of the sample chamber and the convex surface may be arcuately movable relative thereto. In one embodiment the convex surface comprises a motorised cylinder.

The sample chamber may be in the form of a right annular cylinder having the outer wall defined by the concave two dimensional reflector surface and flat end walls. A movable inner cylinder which defines a two dimensional convex surface may be supported for relative rotation by suitable journal bearings and driven by a coaxial stepper motor on the outside of the chamber.

Preferably the energy beam is provided by an infrared source, and a detector cell is provided in the exit path from the chamber.

In one preferred embodiment means are provided to launch a diverging beam on the inlet path. Divergence can be obtained by a simple convex/concave lens arrangement between the infra-red source and the inlet path. It can be demonstrated mathematically that in the plane of a sample cell having circular concentric inner and outer reflection surfaces, a beam of known divergence will reflect from the outer reflector as a convergent beam, and will strike the inner reflector with a beam width which is substantially the same as the incident beam width. Moreover the next reflection from the outer reflector will step around the inner reflector by an angle which is substantially identical to the angle of the first reflection. This property is extremely useful in a practical gas detector since beam divergence in the plane of the arcuate beam path is virtually eliminated and it is relatively easy to calculate actual beam length because each reflection steps the beam around the inner reflector by a constant angle. This latter factor is not true of many prior art sample cells having concave reflectors.

The divergent incident beam reduces loss of signal in the plane of the beam path, but cannot prevent beam scatter due to divergence in the direction perpendicular to the beam path. This difficulty can be overcome by passing the incident beam through a cylindrical lens prior to reflection to thereby eliminate divergence out of the plane of the beam path.

In another preferred embodiment the infra-red beam is collimated by a convex/concave lens arrangement so that the incident beam is cylindrical and has no divergence in any plane. Reflection from the outer reflector with such a beam would result in beam divergence and loss of signal in the plane of the beam path. Accordingly a reflector lens in the incident beam path is provided to reflect the collimated beam convergently towards the inner reflector. By appropriate choice of the additional reflector lens, which is in the form of a two dimensional curve only, the beam thereafter behaves as the divergent/convergent beam described above, but without substantial loss of signal in the direction perpendicular to the beam path.

Where the inner (convex) reflector is arcuately movable or rotatable the additional reflector lens may be mounted on a radially extending arm of the inner reflector.

In the case where the concave and convex reflectors are part spherical, the need for additional optical elements is eliminated since divergence of the incident beam in the direction generally perpendicular to the reflection plane will be corrected by the spherical surface of the concave reflector. Thus a divergent incident beam will become a convergent reflected beam, and beam scatter/signal loss is dramatically reduced.

The inner reflector may house the infra-red source, for example a low voltage bulb connected to an adjacent power source. The bulb may remain stationary whilst the inner reflector moves arcuately; alternatively the bulb may move with the inner reflector provided that rotation end stops prevent undue twisting of connection wires or electrical connection is provided by slip rings or the like. The bulb may include a beam collimator which may be adjustable to give a convergent, parallel or divergent incident beam.

As an alternative the infra-red source may be located outside the sample chamber and the beam may be reflected in through the inner reflector by mirrors or by a periscope lens arrangement.

The inner reflector may include a vane located immediately aft of the inlet path and extending between the inner reflector and the outer reflector—such a vane is useful in quickly sweeping a sample from the chamber and introducing a flushing charge. The vane may comprise a radially extending arm on which additional optical elements may be mounted.

The sample chamber may include more than one inlet path and more than one outlet path. The paths may be coplanar, or alternatively the paths may be provided in different planes. In one embodiment the sample chamber defines two inlet paths in spaced parallel planes. The position of the inlet paths may be chosen to give different path lengths (suitable for detection of different gases) but the beams may leave the chamber in a common exit plane for transmission to separate detectors. Alternatively more than one exit path may be provided.

In another embodiment the inlet paths may be in a common plane but aligned to direct the beam in a different arcuate direction. Once again different path lengths may be provided to suit different gases, and the beams may exit along a substantially common exit path, or along different exit paths.

A combination of these arrangements can give many different path lengths within a closely confined space and without risk of beam interference. In each case the inlet and exit paths may be interchanged.

A shutter may be provided to close one or more of several inlet paths. In the preferred embodiment the shutter may be in the form of a cylinder within the inner reflector and having one or more openings which may be aligned with a desired beam inlet path; such a cylindrical shutter may be rotated by a stepper motor, for example.

The detector cell usually comprises a filter to pass only wavelengths of the beam which are in the desired range, and a sensor which detects absorption of beam energy.

According to another aspect of the invention the chamber may include a plurality of filters movable one at a time into the exit path. Preferably the filters are rotatably mounted on a disc to permit a desired filter to be positioned in an exit path of the sample chamber. Such an arrangement is useful where several beams may have a common exit path, and control logic may be provided to determine the initial position of any beam in the exit path.

The disc may be rotated by a stepper motor to the desired position, and may furthermore be oscillated between filters where more than one gas is to be detected. Adjacent filters may be separated by blocking means which prevent transmission of the energy beam to the detector cell, thus providing the usual chopping function to ensure effective sampling of the beam.

A diffraction grating may be used instead of a filter in the exit path to detect infra-red absorption throughout the spectrum—such an arrangement is useful for a laboratory instrument.

In a further embodiment one or more filters may be included in the cylindrical shutter mentioned above; in this way the incident beam can be confined to desired wavelengths rather than filtering the beam in the exit path.

Other aspects of the invention will be apparent from the following description of a preferred embodiment shown by way of example only with respect to the accompanying drawings in which.

Figures 1, 3:
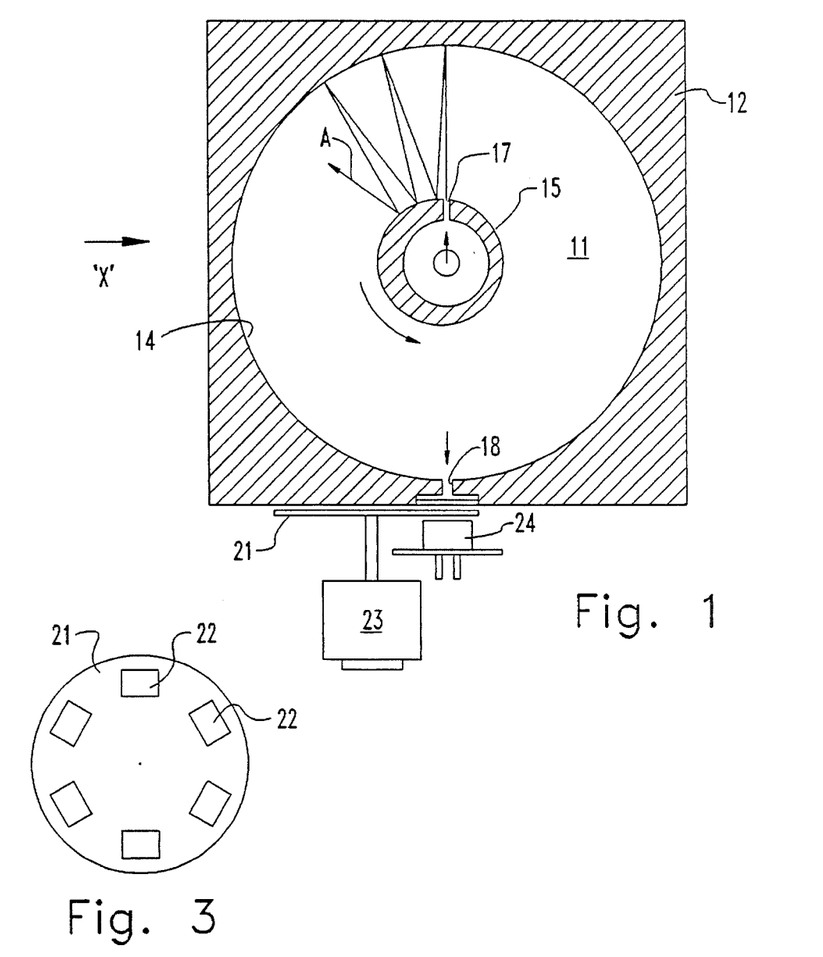
FIG. 1 illustrates a somewhat schematic partial section through a gas detector incorporating a sample chamber according to a first preferred embodiment of the invention.
FIG. 3 illustrates in elevation the rotatable filter disc.
Figure 2:
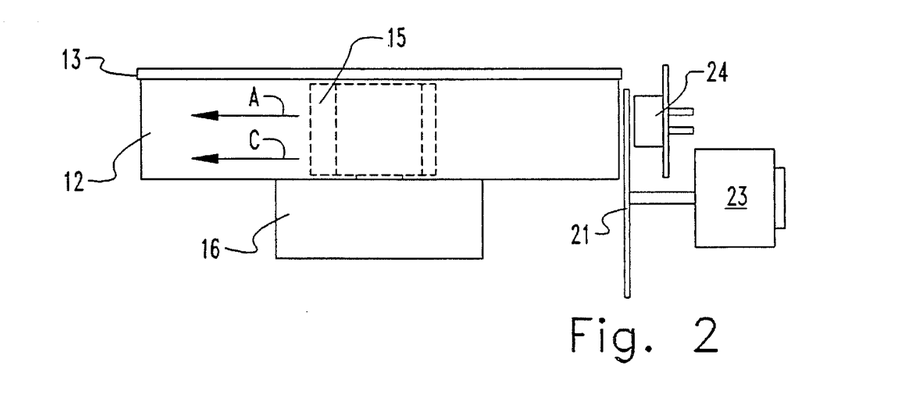
FIG. 2 is an elevation of the detector of FIG. 1 in the direction of arrow X.

With reference to the drawings an infra-red gas detector 10 comprises a sample chamber 11 defined by a housing 12 and a lid 13. The sample chamber has a gas charging port and a gas discharging port (not shown), of any suitable type. The chamber 11 is in the form of a right cylinder having a circular outer wall 14 and end faces at right angles thereto. Coaxial within the chamber is an inner cylinder 15 rotatable about its longitudinal axis by a stepper motor 16. The inner cylinder 15 comprises a peripheral wall having an inlet opening 17 which defines a non radial inlet path for an infra-red beam. In this embodiment the infra-red beam is provided by a light bulb, which may be located within the inner cylinder 15, or outside the chamber in which case the beam is directed to the inlet path via an arrangement of mirrors.

The outer wall 14 has an exit opening 18 which defines an exit path for the infra-red beam.

A rotatable disc 21 has a number of filters 22, and is rotatable by a stepper motor 23 to bring a desired filter into the exit path from the sample chamber. The disc 21 lies between the exit opening 18 and an infra-red sensor 24 of any suitable kind.

The filters 22 are of a known kind and designed to restrict the passage of infra-red radiation to a desired range of wavelengths. Different gases absorb infra-red radiation at different wavelengths and in a distinctive pattern. Thus by using an appropriate filter, measuring the passage of infra-red radiation through a control gas sample, and comparing it with the passage of infra-red radiation through a sample of unknown gas, it is possible to determine the presence and concentration of particular gases.

One of the filters or a gap in the disc may be arranged to pass all light as a reference for the sensor 24 and to permit the control mechanism to determine the stepper motor start position.

Figure 4:
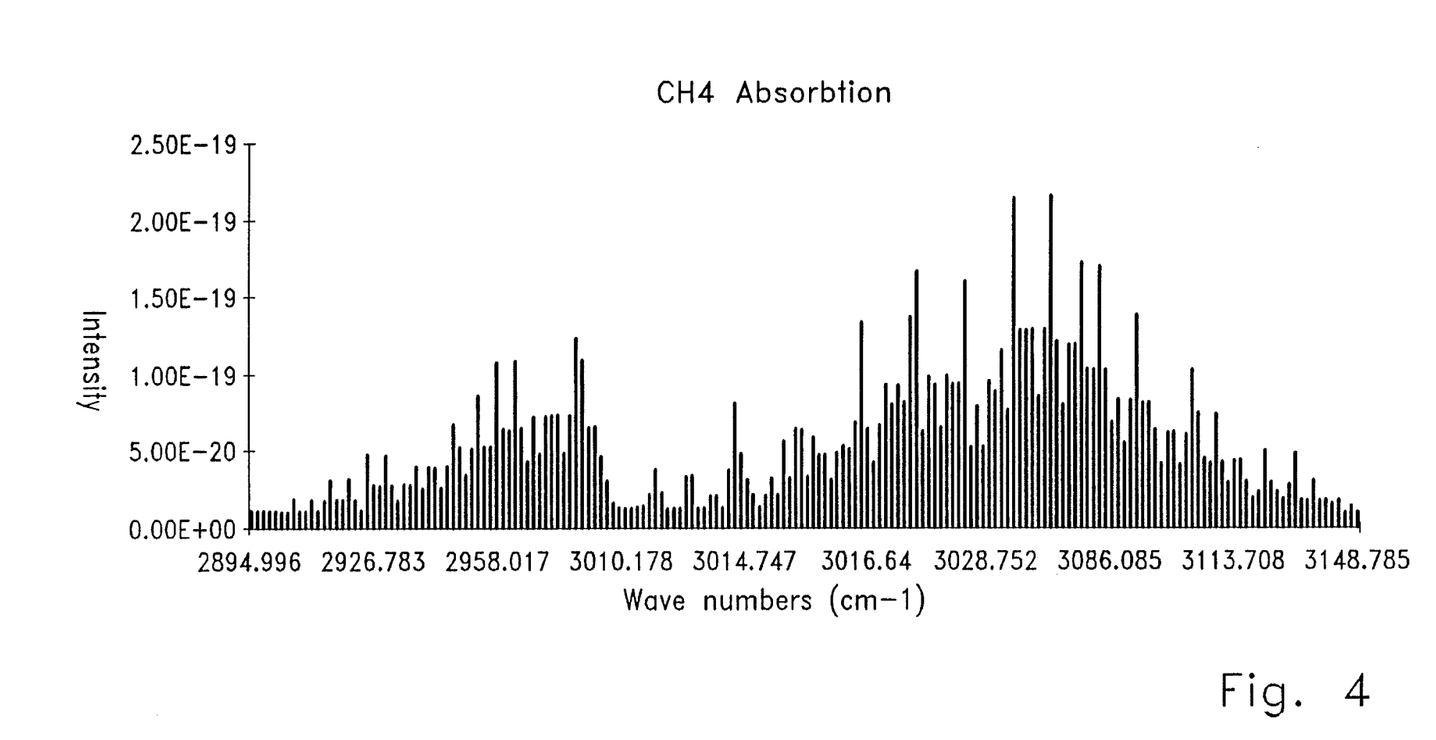
FIG. 4 illustrates the infra-red absorption characteristic for $CH_4$ (methane)
Figure 5:
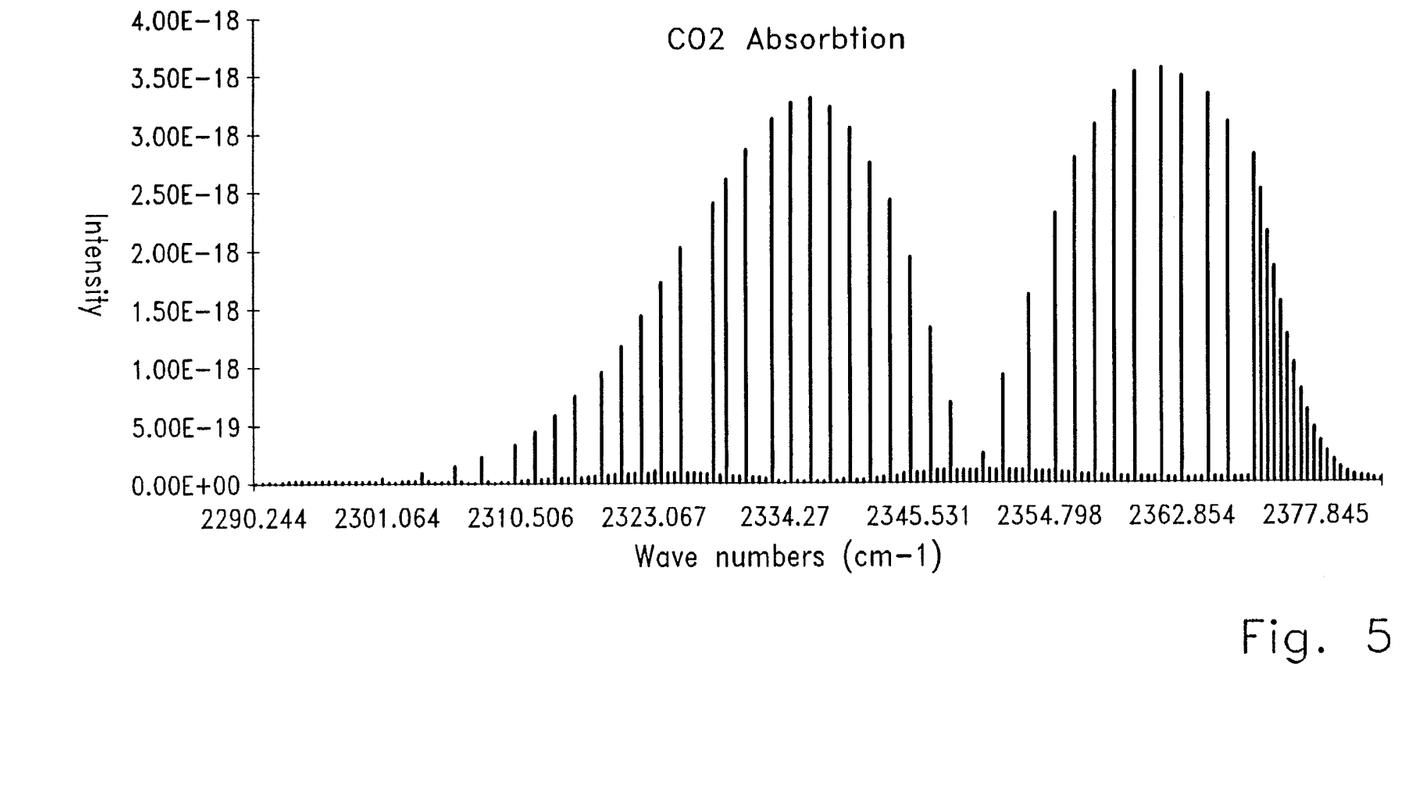
FIG. 5 illustrates the infra-red absorption characteristic for $CO_2$ (carbon dioxide)

FIGS. 4 and 5 show the absorption characteristics of $CH_4$ (methane) and $CO_2$ (carbon dioxide) and illustrate the intensity of absorption (loss of radiation) in a particular range of wave numbers (the inverse of wavelength). By restricting the transmission of the infra-red beam to these respective wave lengths, the presence or absence of $CH_4$ or $CO_2$ and their respective concentrations can be determined by known methods which do not need to be further described here.

The sensor 24 can be of any suitable type, for example a pyroelectric/lead salt detector.

The gas detector is under the control of suitable control apparatus, not shown which includes means to select a particular gas which it is desired to detect, means to cause rotation of the stepper motor 16 to an appropriate start position (thus setting the path length of the infrared beam) and means to cause rotation of the stepper motor 23 to place the correct filter in the exit path of the beam. The control apparatus would typically be computerised, and pre-programmed with all relevant stepper motor settings for the range of gases to be detected. It is envisaged that simple push button selection of a particular gas would be all that is required.

In use, the detector is calibrated in a known manner for the chosen input energy and path lengths. The gas sample is introduced into the chamber 11 through the charging port and the gas to be detected is selected. The inner cylinder 5 is rotated by stepper motor 6 to the appropriate start position such that the beam path length is at the correct position for optimum performance of the detector. The disc 21 is rotated to place the appropriate filter in the beam exit path.

When the infra-red source is switched on, the beam passes through the sample in the manner indicated by arrow A; the concave surface ensures good beam collimation. The sensor detects the absorption of infra-red energy in the relevant wavelengths and thus permits calculation of the concentration of the particular gas, if present, in a known manner. The detector may give a direct read-out by visual display.

The known sensors usually work by alternately permitting the beam to pass, and blocking the beam. This function can be provided by causing the stepper motor to reciprocate the filter disc so that the appropriate filter moves into and out of the exit path of the beam, the adjacent part of the disc being opaque to the beam.

The detector can be arranged to sample for two different gases at once assuming that the beam path length is suitable for both, by reciprocating the disc between one filter and another, the intermediate opaque portions providing the chopping function. With suitable control the inner cylinder could be caused to rotate at the same time as the disc to permit two or more gases to be detected with path lengths set to the appropriate value.

Figure 6:
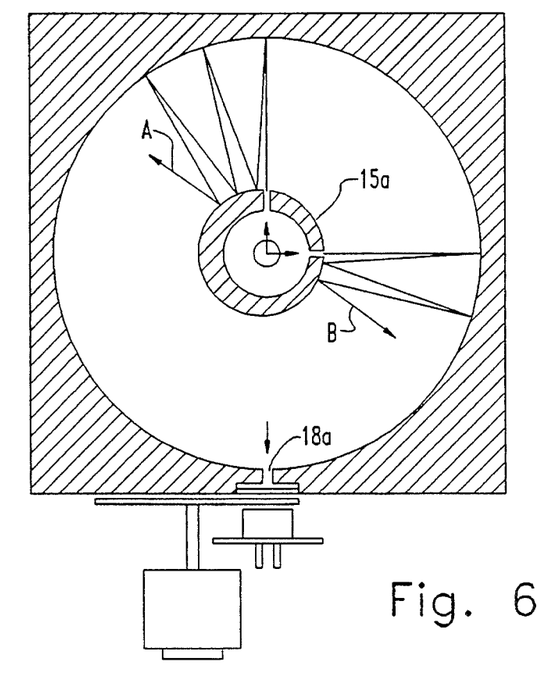
FIG. 6 illustrates a second embodiment of the invention having beams moving in opposite arcuate directions.

FIG. 6 illustrates an embodiment in which the inner cylinder 15a has two apertures positioned to aim light beams in opposite directions around the chamber in parallel planes. The beams have a common exit path 18a but may be directed to different sensors. Blocking means (such as a shutter) may be provided to close one or other aperture as required. The beams are represented by arrows A and B and have different test lengths.

FIG. 2 illustrates an arrangement in which beams may be passed through the sample cell in parallel planes by having spaced inlet paths—the beams are marked A and C. In the example illustrated beam A would pass to detector 24, and beam C would pass through another exit path to a detector positioned elsewhere on the periphery of the housing.

Figure 7:
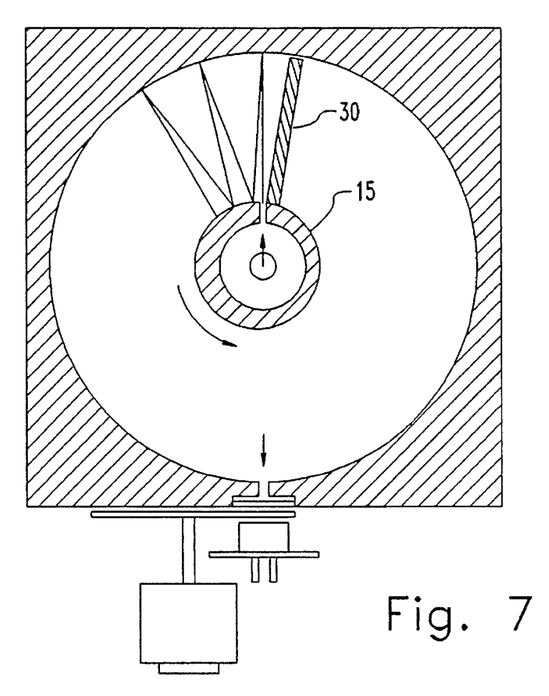
FIG. 7 illustrates a vane for flushing the sample chamber.

FIG. 7 illustrates a detector having a radial vane 30 mounted on the inner cylinder 15 for rotation therewith. Rotation of the inner cylinder after sampling results in the vane flushing gas from the cylinder through an outlet port (not shown), whilst a fresh charge is drawn in through inlet port (not shown). Such an arrangement ensures that new samples are less likely to be contaminated by the residue of an old sample. It is not necessary for the vane to contact the inner surfaces of the sample chamber, merely be a reasonably close fit.

In a typical embodiment the sample chamber is annular and has an external radius of 80 mm and an internal radius of 25 mm. This size is sufficient to give path lengths in the range 30 mm to 2500 mm without increasing the number of reflections to a point where a stepper motor for the inner cylinder is required to step by very small angles. With a narrow beam of good collimation the number of reflections could however be increased substantially, and so lengthen the test distance.

In another embodiment (not illustrated) the beam is reflected around an annular chamber in a first plane and then reflected into a second plane by a mirror arrangement for further reflection around the chamber. In this way the beam can be reflected around the chamber in several planes to increase path length; simple periscope type optics may be used to reflect the beam into another plane.

Figure 8:
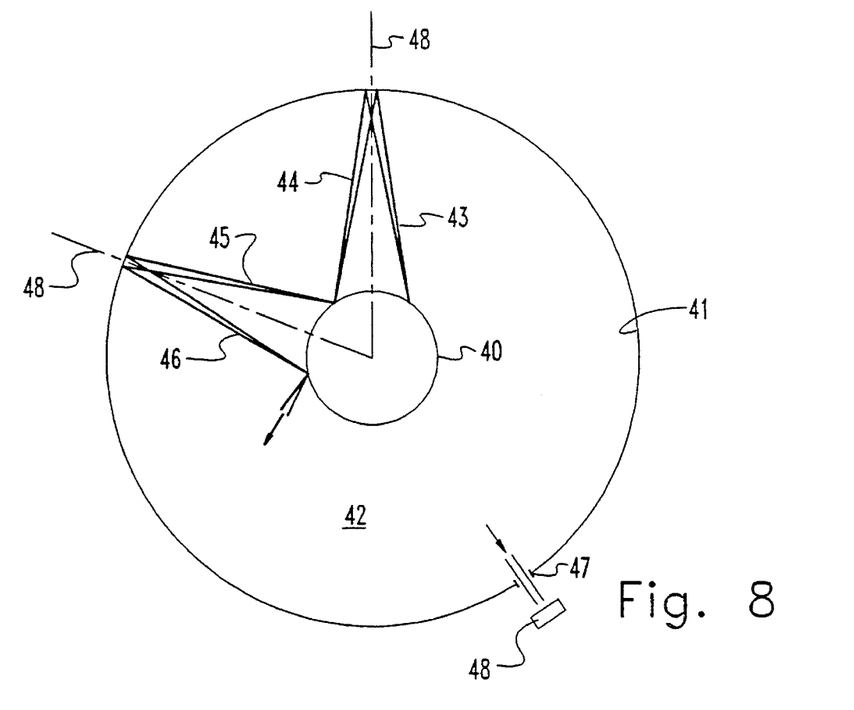
FIG. 8 is an exaggerated reflection diagram of a preferred embodiment having a divergent incident beam.

FIG. 8 illustrates in an exaggerated manner the effect of a diverging beam emanating from an inner cylinder 40 and reflecting from an outer cylinder 41, the space between the cylinders constituting the sample chamber 42.

The diverging beam 43 reflects back from the outer cylinder 41 as a reflected beam 44, the curvature of the outer cylinder 4 causes the beam to converge, and by appropriate choice of dimensions the reflected beam impinges on the inner cylinder 40 with the same beam width as the incident beam. Thus loss of signal due to divergence in the plane of the beam path is substantially eliminated. A further reflection is illustrated by diverging beam 45 and converging beam 46 the beam continues reflecting until it reaches an exit path 47 and sensor 48 (illustrated schematically).

A further feature of this arrangement is that the angle through which each reflection passes is substantially identical, since each diverging and converging beam makes the same angle with a radial line 48. This renders calculation of the beam test length straightforward, unlike manner prior art arrangements where reflection distances change for each reflection.

In practice the angle of the incident beam would be such as to give around 100 reflections for a beam which passed through 360° around the sample chamber.

Figure 9:
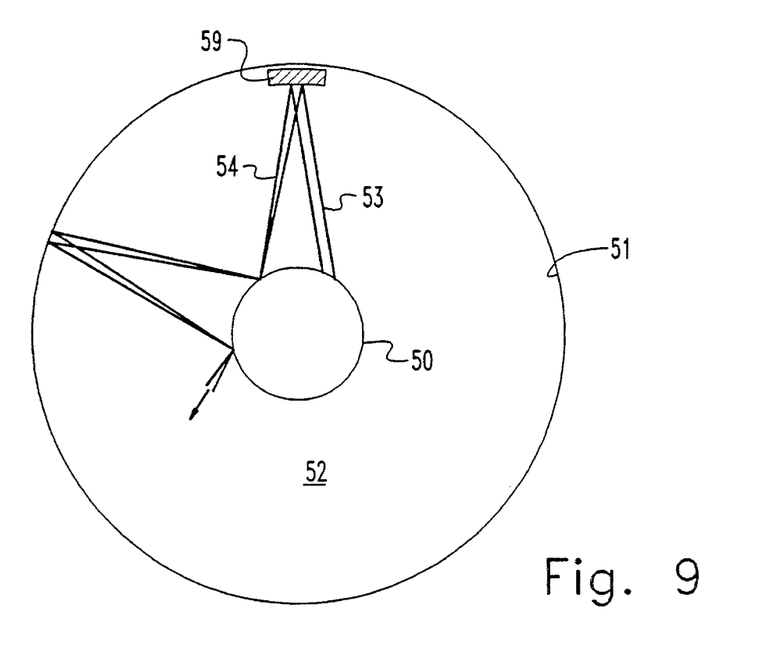
FIG. 9 is an exaggerated reflection diagram of a preferred embodiment having a collimated incident beam.

FIG. 9 illustrates an alternative embodiment in which a fully collimated beam 53 emanates from the inner cylinder 50 through the sample chamber 52. A collimated beam has no divergence and thus substantially no loss of signal in the plane of the beam path as it proceeds around the sample chamber. A reflector lens 59 between the inner and outer cylinders 50,51 reflects the collimated beam 53 as a converging beam 54 and is designed to ensure that the beam 54 impinges on the inner cylinder 50 with a beam width and position equivalent to that of the first reflection illustrated in FIG. 8. Thereafter the beam behaves as that illustrated in FIG. 8 but without substantial divergence in the plane of the beam. Signal loss is thus substantially reduced.

The reflector lens 59 is typically a single curvature mirror and may be mounted on a radial arm of the inner cylinder, such as the radial arm 30 illustrated in FIG. 7. The reflector lens need only be wide enough to reflect the collimated beam, and where a very small change of angle on reflection is provided (for example, less than 1°) the lens will clearly be quite narrow.

Because the angular steps of the beam around the inner cylinder are equal, no re-alignment of the lens 59 is required in the case where the inner cylinder 50 is arcuately movable. This is a particular advantage over prior art reflection arrangements where the reflection distance often changes after each reflection.

The design of lenses, the method of beam collimation, and the method of producing a divergent beam of the appropriate characteristics are conventional matters and need not be further described in this application.

Beam scatter due to divergence out of the plane of the beam path can be dealt with by passing the beam through a cylindrical lens prior to reflection thereby confining the beam to a substantially single plane.

Figure 10:
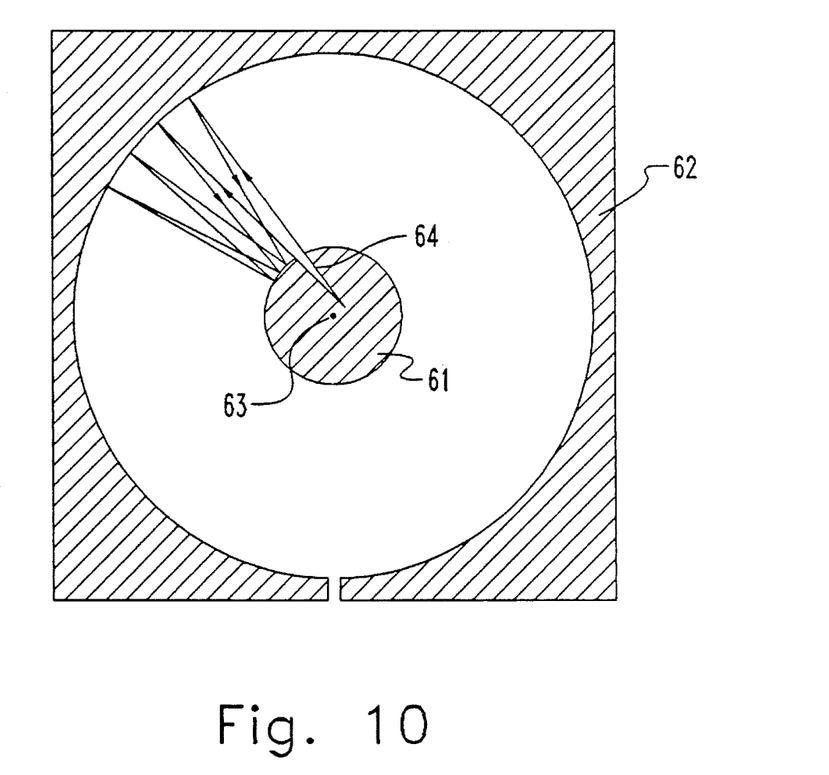
FIG. 10 illustrates a somewhat schematic horizontal section through a third embodiment of the invention having part-spherical reflectors.
Figure 11:
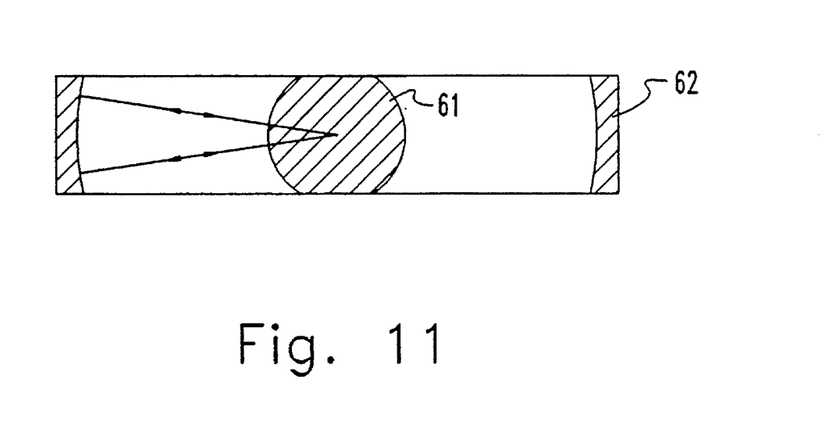
FIG. 11 is a vertical section through the embodiment of FIG. 10.

An alternative arrangement which eliminates the potential problem of beam scatter out of the plane of the beam path is illustrated in FIGS. 10 and 11. Convex and concave reflectors 61,62 have a common centre 63. A divergent beam 64, launched off-centre to ensure progressive reflection, diverges in all planes, but reflection from the concave part-spherical reflector 62 ensures that the beam is focused on the convex reflector 6 with a spot size substantially the same as that of the incident beam (as illustrated in FIG. 11).

Such an arrangement may have relatively rotatable convex and concave reflectors as previously described.

Other arrangements are possible within the scope of the claims appended hereto.

I claim:

1. A sample chamber for a gas detector, the chamber having a gas sample inlet, and defining an inlet path for a beam of energy, an exit path for said beam of energy and reflector means whereby said beam of energy is in use reflected from said inlet path to said exit path, said reflector means including a concave reflector surface and a convex reflector surface.

2. The chamber of claim 1 wherein the concave and convex surfaces are movable relative to each other to change the path length between the inlet path and the outlet path.

3. The chamber of claim 2 wherein the concave and convex surfaces are movable arcuately with respect to one another.

4. The chamber of claim 3 wherein the surfaces are cylindrical.

5. The chamber of claim 4 wherein the surfaces are relatively rotatable about a common axis.

6. The chamber of claim 3 wherein the surfaces are spherical or part spherical.

7. The chamber of claim 6 wherein the surfaces are relatively rotatable about a common centre.

8. The chamber of claim 4 further including a vane extending radially from one of the concave and convex surfaces and sealingly engaging the other of the concave and convex surfaces.

9. The chamber of claim 1 wherein the inlet path is defined by an inlet opening in the convex reflector surface and the outlet path is defined by an outlet opening in the concave reflector surface.

10. The chamber of claim 9 further including an infra-red source upstream of said inlet opening.

11. The chamber of claim 10 further including an optical collimator for said beam, the collimator being located upstream of a first reflection surface.

12. The chamber of claim 11 wherein said coillimator is adapted to give a substantially cylindrical beam.

13. The chamber of claim 1 and having more than one inlet opening.

14. The chamber of claim 1 and having more than one outlet opening.

15. The chamber of claim 13 and further including a shutter to close one or sore of said inlet openings.

16. The chamber of claim 1 and further including a plurality of filters movable one at a time into said outlet path.

17. The chamber of claim 16 wherein said filters are rotatably mounted on a disc.

18. The chamber of claim 1 and further including a detector cell in said outlet path.

19. The chamber of claim 14 and further including a shutter to close one or more of said outlets openings.

* * * * *